(12) United States Patent
Goorevich et al.

(10) Patent No.: US 11,722,826 B2
(45) Date of Patent: *Aug. 8, 2023

(54) HIERARCHICAL ENVIRONMENTAL CLASSIFICATION IN A HEARING PROSTHESIS

(71) Applicant: Cochlear Limited, Macquarie University (AU)

(72) Inventors: Michael Goorevich, Naremburn (AU); Obaid ur Rehman Qazi, Mechelen (BE); Carl Puchner, Narraweena (AU)

(73) Assignee: Cochlear Limited, Macquarie University (AU)

( * ) Notice: Subject to any disclaimer, the term of this patent is extended or adjusted under 35 U.S.C. 154(b) by 0 days.

This patent is subject to a terminal disclaimer.

(21) Appl. No.: 17/731,832

(22) Filed: Apr. 28, 2022

(65) Prior Publication Data
US 2022/0312130 A1  Sep. 29, 2022

Related U.S. Application Data

(63) Continuation of application No. 16/755,744, filed as application No. PCT/IB2018/057847 on Oct. 10, 2018, now Pat. No. 11,337,011.
(Continued)

(51) Int. Cl.
*H04R 25/00* (2006.01)
*A61N 1/36* (2006.01)

(52) U.S. Cl.
CPC ......... *H04R 25/50* (2013.01); *A61N 1/36036* (2017.08); *H04R 25/75* (2013.01); *H04R 2225/41* (2013.01)

(58) Field of Classification Search
CPC .................................................. A61N 1/36036
See application file for complete search history.

(56) References Cited

U.S. PATENT DOCUMENTS

| 7,738,667 | B2 | 6/2010 | Bramsløw |
| 9,364,669 | B2 | 6/2016 | Kehtarnavaz |

(Continued)

FOREIGN PATENT DOCUMENTS

| CN | 1813491 A | 8/2006 |
| CN | 101515454 A | 8/2009 |

(Continued)

OTHER PUBLICATIONS

International Search Report and Written Opinion received in related international application No. PCT/IB2018/057847, dated Feb. 1, 2019 (16 pages).

(Continued)

*Primary Examiner* — Mark Fischer
(74) *Attorney, Agent, or Firm* — Edell, Shapiro & Finnan, LLC

(57) ABSTRACT

Presented herein are techniques for generating a hierarchical classification of a set of sound signals received at hearing prosthesis. The hierarchical classification includes a plurality of nested classifications of a sound environment associated with the set of sound signals received at hearing prosthesis, including a primary classification and one or more secondary classifications that each represent different characteristics of the sound environment. The primary classification represents a basic categorization of the sound environment, while the secondary classifications define subcategories/refinements of the associated primary classification and/or other secondary classifications.

20 Claims, 12 Drawing Sheets

Related U.S. Application Data

(60) Provisional application No. 62/573,226, filed on Oct. 17, 2017.

(56) References Cited

U.S. PATENT DOCUMENTS

| | | | |
|---|---|---|---|
| 11,337,011 B2* | 5/2022 | Goorevich | ............ H04R 25/75 |
| 2002/0191799 A1 | 12/2002 | Nordqvist | |
| 2014/0336448 A1 | 11/2014 | Banna | |
| 2016/0158546 A1 | 6/2016 | Fredelake | |
| 2018/0012614 A1 | 1/2018 | Soleymani et al. | |
| 2018/0125415 A1 | 5/2018 | Reed et al. | |

FOREIGN PATENT DOCUMENTS

| | | |
|---|---|---|
| CN | 102088648 A | 6/2011 |
| EP | 2328363 B1 | 5/2016 |
| WO | 2016162758 A1 | 10/2016 |

OTHER PUBLICATIONS

Zhang, Tony, et al., "Hierarchical Classification of Audio Data For Archiving and Retrieving," 1999 IEEE International Conference on Acoustics, Speech and Signal Processing, Mar. 19, 1999 (4 pages).

* cited by examiner

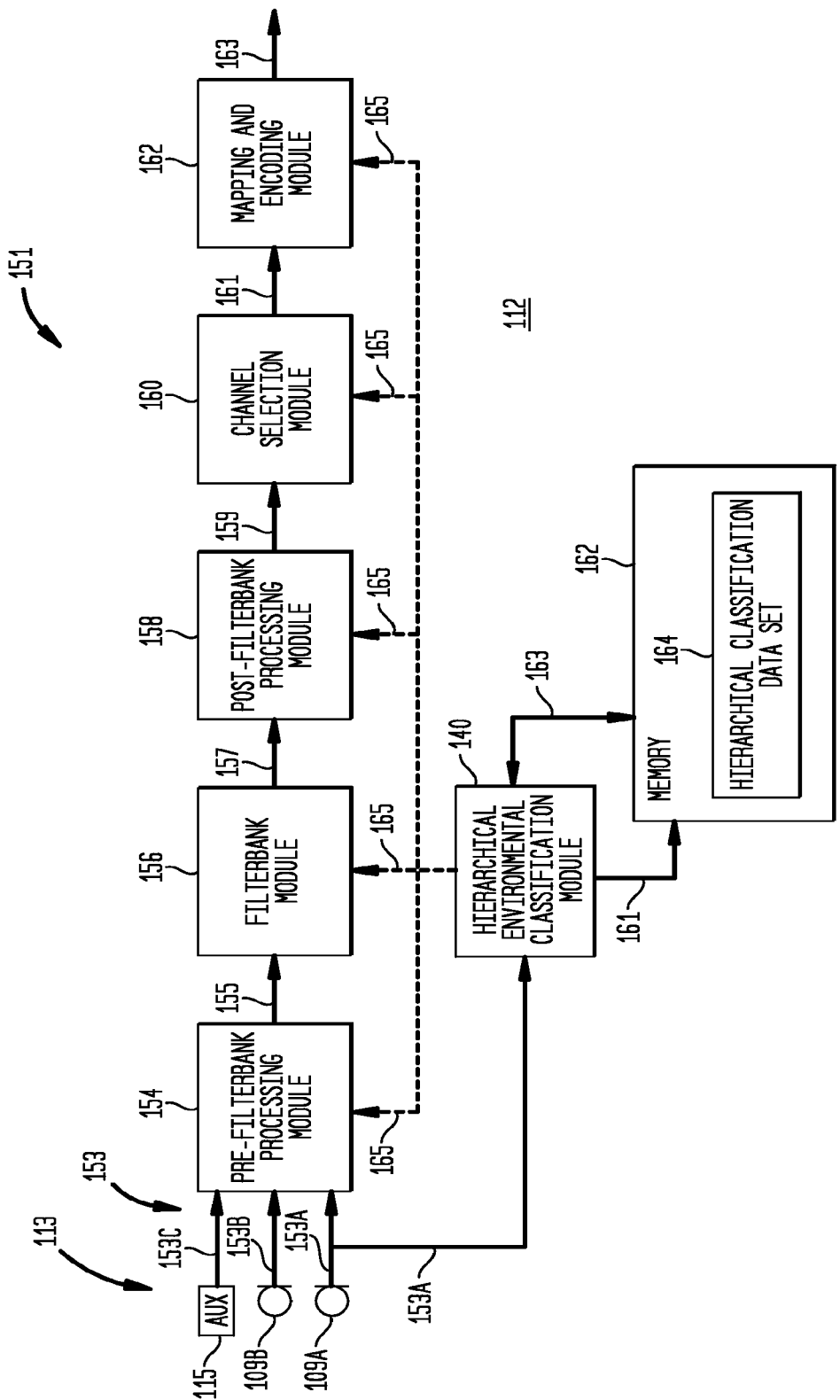

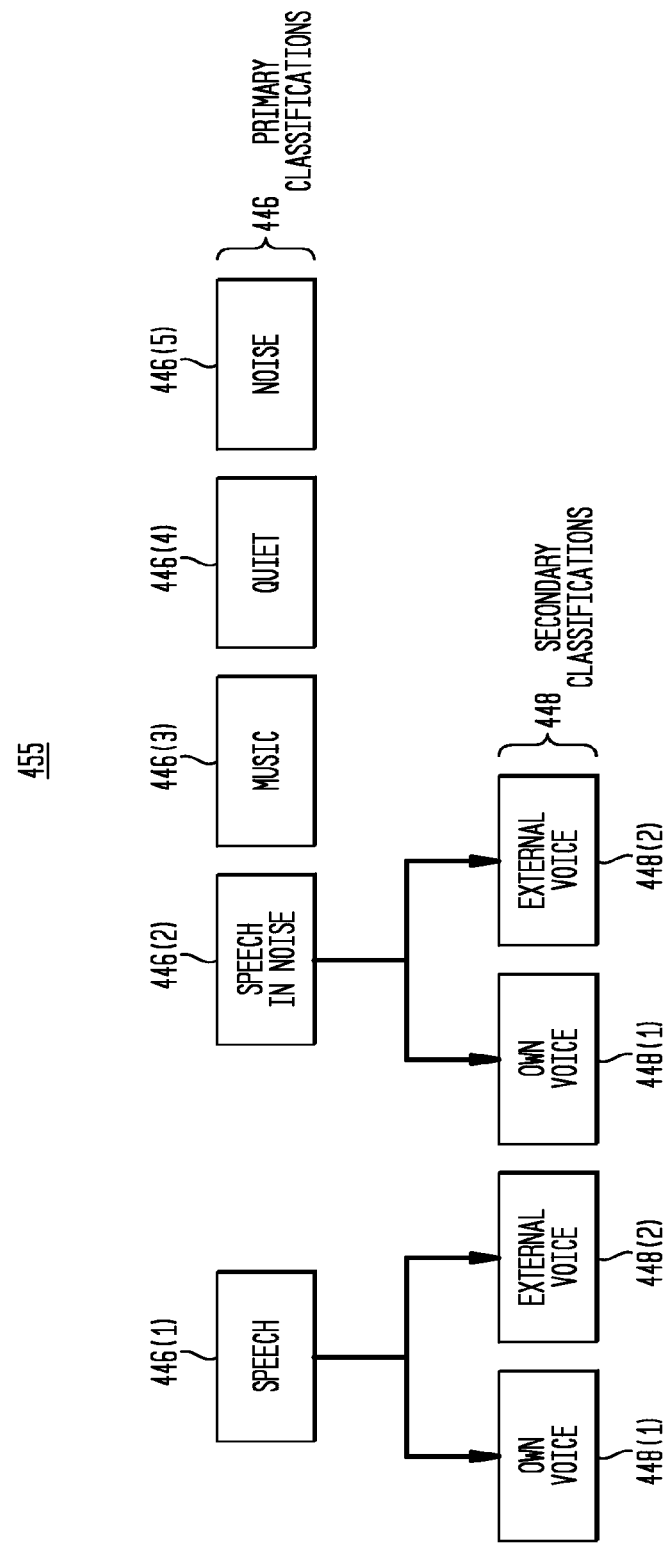

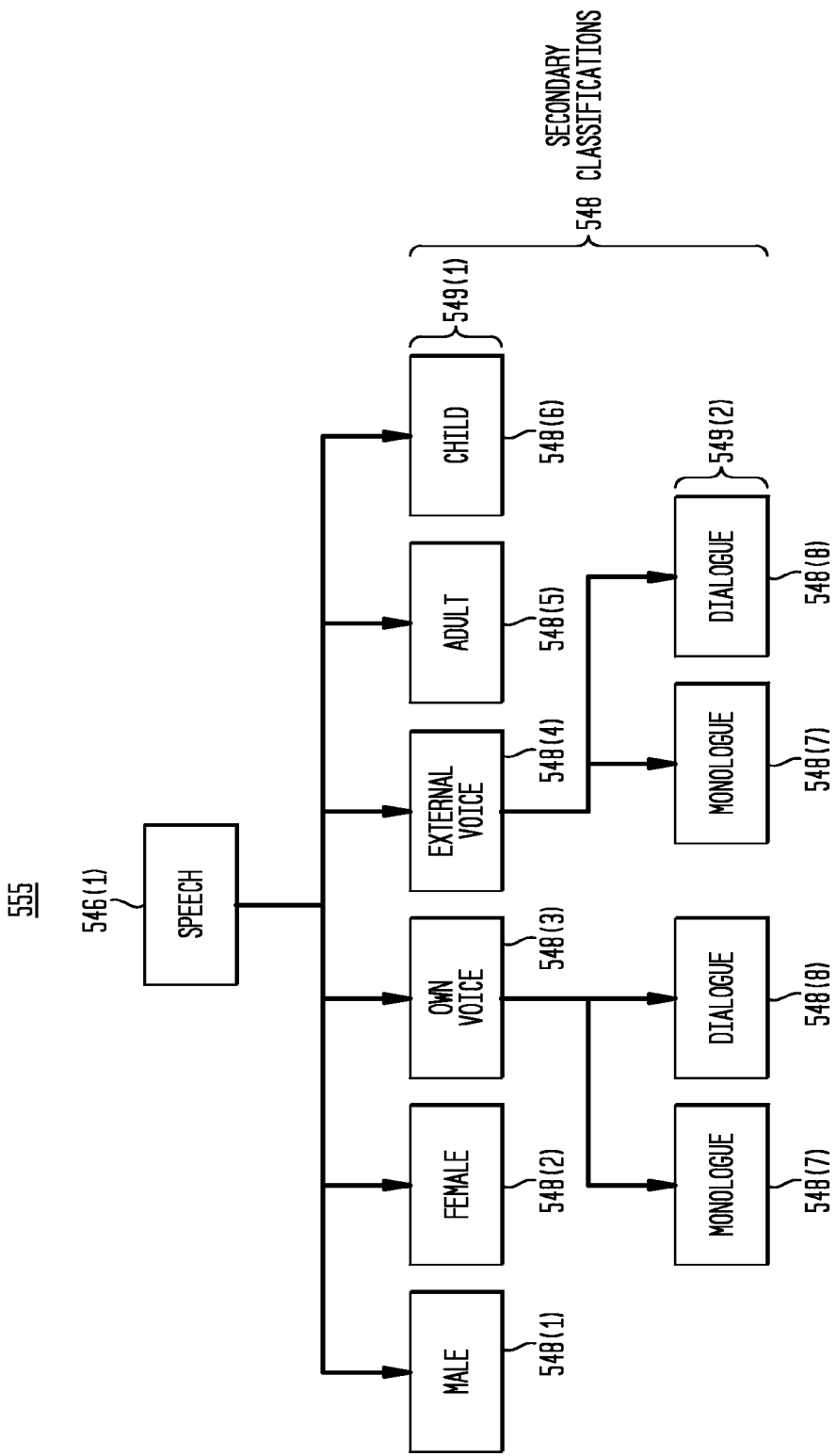

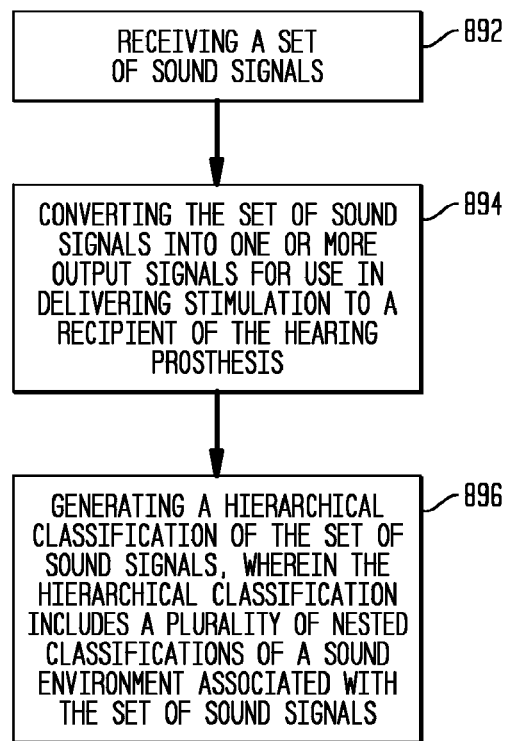

HIERARCHICAL ENVIRONMENTAL CLASSIFICATION IN A HEARING PROSTHESIS

BACKGROUND

Field of the Invention

The present invention relates generally to hierarchical environmental classification in a hearing prosthesis.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. An auditory brainstem stimulator is another type of stimulating auditory prosthesis that might also be proposed when a recipient experiences sensorineural hearing loss due to damage to the auditory nerve.

Certain individuals suffer from only partial sensorineural hearing loss and, as such, retain at least some residual hearing. These individuals may be candidates for electro-acoustic hearing prostheses.

SUMMARY

In one aspect, a method is provided. The method comprises: at a hearing prosthesis: receiving a set of sound signals; determining, from the set of sound signals, a primary classification of a current sound environment associated with the sound signals; and determining, from the set of sound signals, one or more secondary classifications of the current sound environment, wherein the one or more secondary classifications are derivative of the primary classification.

In another aspect, a hearing prosthesis is provided. The hearing prosthesis comprises: one or more input elements configured to receive at least one set of sound signals; a memory; and one or sound input processors coupled to the memory and the one or sound input elements, and configured to: convert the set of sound signals into one or more output signals for use in delivering stimulation to a recipient of the hearing prosthesis, and generate a hierarchical classification of the at least one set of sound signals, wherein the hierarchical classification includes a plurality of nested classifications of a sound environment associated with the at least one set of sound signals.

In another aspect, a method is provided. The method comprises: at a hearing prosthesis: receiving a set of sound signals; converting the set of sound signals into one or more output signals for use in delivering stimulation to a recipient of the hearing prosthesis; and generating a hierarchical classification of the set of sound signals, wherein the hierarchical classification includes a plurality of nested classifications of a sound environment associated with the sound signals.

BRIEF DESCRIPTION OF THE DRAWINGS

Embodiments of the present invention are described herein in conjunction with the accompanying drawings, in which:

FIG. 3A is a functional block diagram illustrating further details of a hearing prosthesis configured to implement the hierarchical environmental classification techniques presented herein;

FIG. 4A is a schematic diagram of a hierarchical classification structure that may be implemented by a hierarchical environmental classification module, in accordance with embodiments presented herein;

FIGS. 5 and 6 are schematic diagrams illustrating example secondary classifications, in accordance with certain embodiments presented herein;

FIG. 8 is a flowchart of another method, in accordance with certain embodiments presented herein.

DETAILED DESCRIPTION

Presented herein are techniques for generating a hierarchical classification of a set of sound signals received at hearing prosthesis. The hierarchical classification includes a plurality of nested classifications of a sound environment associated with the set of sound signals. The sound environment associated with the set of sound signals may be the ambient environment in which the hearing prosthesis is located (i.e., when the sound signals are ambient sound signals) and/or a non-ambient sound environment (i.e., when the sound signals are non-ambient sound signals received, for example, wireless audio signals, etc.). The plurality of nested classifications of the sound environment include a primary classification and one or more secondary classifications that each represents a different characteristic of the sound environment. The primary classification represents a basic categorization of the sound environment, while the secondary classifications define sub-categories/refinements of the associated primary classification and/or other secondary classifications.

There are a number of different types of hearing prostheses in which embodiments of the present invention may be implemented. However, merely for ease of illustration, the techniques presented herein are primarily described with reference to one type of hearing prosthesis, namely a cochlear implant. It is to be appreciated that the techniques presented herein may be used in other hearing prostheses, such as auditory brainstem stimulators, hearing aids, electro-acoustic hearing prostheses, etc.

Figure 1A:
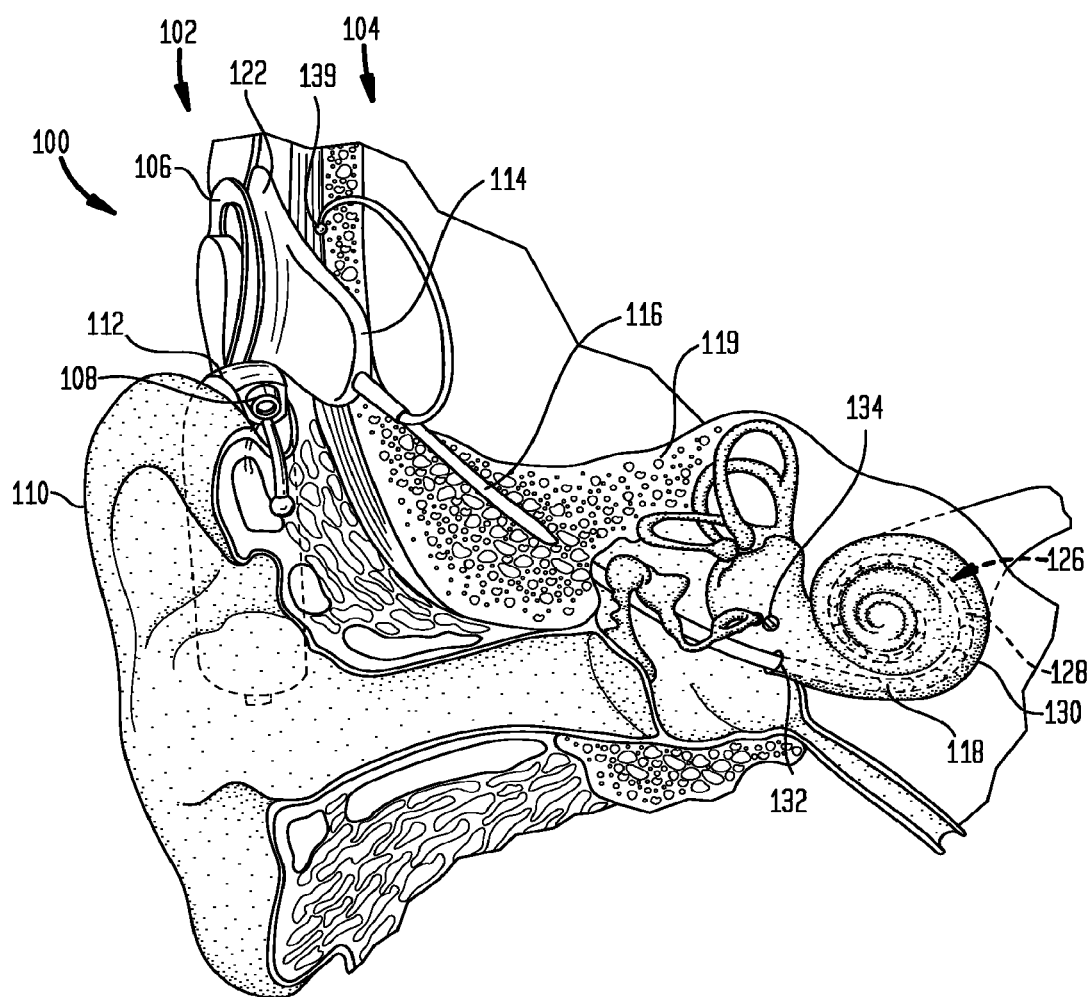
FIG. 1A is a schematic diagram illustrating a cochlear implant, in accordance with certain embodiments presented herein.
Figure 1B:
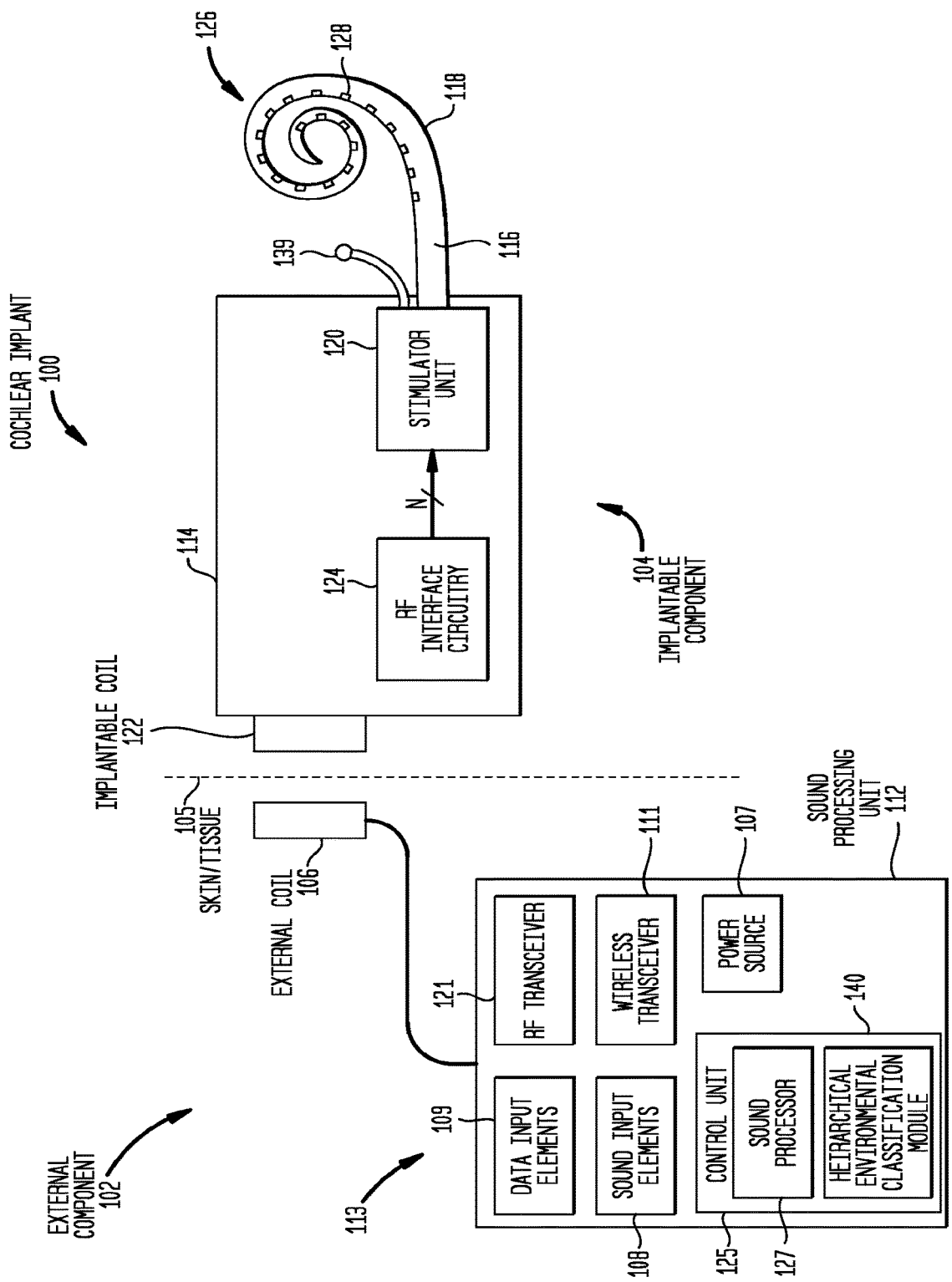
FIG. 1B is a block diagram of the cochlear implant of FIG. 1A.

FIG. 1A is a schematic diagram of an exemplary cochlear implant 100 configured to implement embodiments of the present invention, while FIG. 1B is a block diagram of the cochlear implant 100. For ease of illustration, FIGS. 1A and 1B will be described together.

The cochlear implant 100 comprises an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more input elements 113 for receiving sound signals at a sound processing unit 112. In this example, the one or more one or more input elements 113 include sound input elements 108 (e.g., microphones positioned by auricle 110 of the recipient, telecoils, etc.), data input elements 109 (e.g., Universal Serial Bus (USB) ports, cable ports, etc.), and a wireless transceiver 111 (e.g., to receive wireless sound/audio signals), each located in, on, or near the sound processing unit.

The sound processing unit 112 also includes, for example, at least one battery 107, a radio-frequency (RF) transceiver 121, and a control unit 125. The control unit 125 includes a sound processor 127 and a hierarchical environmental classification module 140. The sound processor 127 is configured to covert electrical signals generated by the sound inputs 108 into processed signals 131.

As described further below, the hierarchical environmental classification module 140 is configured to evaluate/analyze attributes of a set of sound signals received by the one or more input elements (e.g., sound input element 108) of the cochlear implant 100. Based on the analysis of the set of sound signals, the hierarchical environmental classification module 140 is configured to generate a "hierarchical classification" of (for) the set of sound signals. The hierarchical classification may include a primary classification of the sound environment of the cochlear implant 100 and one or more associated secondary classifications that are derivative of the primary classification. That is, the one or more secondary classifications are encompassed by the associated primary classification and sub-categorize the primary classification.

The implantable component 104 comprises an internal/implantable coil 122, an implant body 114, a lead region 116, and an elongate intra-cochlear stimulating assembly 118. As shown in FIG. 1B, the implant body 114 comprises a stimulator unit 120 and radio-frequency (RF) interface circuitry 124. The RF interface circuitry 124 is connected to the implantable coil 122 and, generally, a magnet (not shown) fixed relative to the internal coil 122.

The magnets in the external component 102 and implantable component 104 facilitate the operational alignment of the external coil 106 with the implantable coil 122. The operational alignment of the coils enables the implantable coil 122 to receive power and/or data to/from the external coil 106. More specifically, in certain examples, RF transceiver 121 is configured to transmit electrical signals (e.g., power and data) to implantable coil 122 via an RF link between external coil 106 and implantable coil 122. Implantable coil 122 is typically a wire antenna coil comprised of multiple turns of electrically insulated single-strand or multi-strand platinum or gold wire. The electrical insulation of implantable coil 122 is provided by a flexible molding (e.g., silicone molding). Various other types of energy transfer, such as infrared (IR), electromagnetic, capacitive and inductive transfer, may be used to transfer the power and/or data from an external device to a cochlear implant and, as such, FIGS. 1A and 1B illustrate only one example arrangement.

Elongate stimulating assembly 118 is configured to be at least partially implanted in cochlea 130 and includes a plurality of longitudinally spaced intra-cochlear electrical stimulating contacts (electrodes) 128 that collectively form a contact array 126. Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120.

As noted, the sound processor 127 in sound processing unit 112 is configured to execute sound processing and coding to convert a detected sound into processed sound signals 131. These processed sound signals 131 and are sent to the implantable component 104 via the RF link between external coil 106 and implantable coil 122. The stimulator unit 120 is configured to utilize the processed sound signals 131 to generate electrical stimulation signals that are delivered to the recipient's cochlea via one or more stimulating contacts 128. In this way, the cochlear implant stimulates the recipient's auditory nerve cells, bypassing absent or defective hair cells that normally transduce acoustic vibrations into neural activity.

Figure 1C:
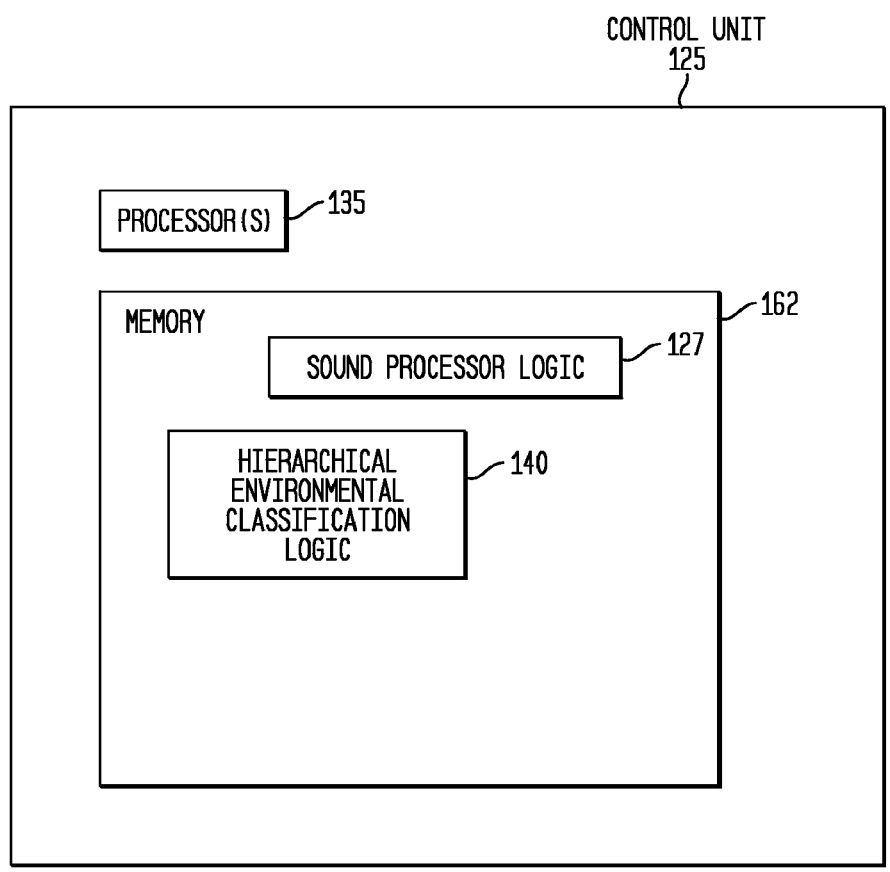
FIG. 1C is a schematic diagram illustrating one embodiment of a control unit of the cochlear implant of FIG. 1A that is configured to implement the hierarchical environmental classification techniques presented herein.

As noted, the sound processing unit 112 includes control unit 125 which comprises sound processor 127 and hierarchical environmental classification module 140. FIG. 1C is a diagram illustrating one arrangement for control unit 125, in accordance with certain embodiments presented herein. In this example, the control unit 125 includes one or more processors 135 and a memory 162. The memory 162 includes sound processor logic 127 and hierarchical environmental classification logic 140. That is, in this example, the sound processor 127 and the hierarchical environmental classification module 140 are implemented as software elements of the control unit 125. As described further below, the memory 162 may also store other data associated with the hierarchical environmental classification module 140.

The memory 162 may be read only memory (ROM), random access memory (RAM), or another type of physical/tangible memory storage device. Thus, in general, the memory 185 may comprise one or more tangible (non-transitory) computer readable storage media (e.g., a memory device) encoded with software comprising computer executable instructions (i.e., sound processor logic 127 and hierarchical environmental classification logic 140) that, when the software is executed by the one or more processors 135, the one or more processors are operable to perform the operations described herein with reference to the sound processor 127 and the hierarchical environmental classification module 140.

As noted, FIG. 1C illustrates software implementations for the sound processor 127 and the hierarchical environmental classification module 140. However, it is to be appreciated that one or more operations associated with the sound processor 127 and the hierarchical environmental classification module 140 may be partially or fully implemented with digital logic gates in one or more application-specific integrated circuits (ASICs).

Figure 2:
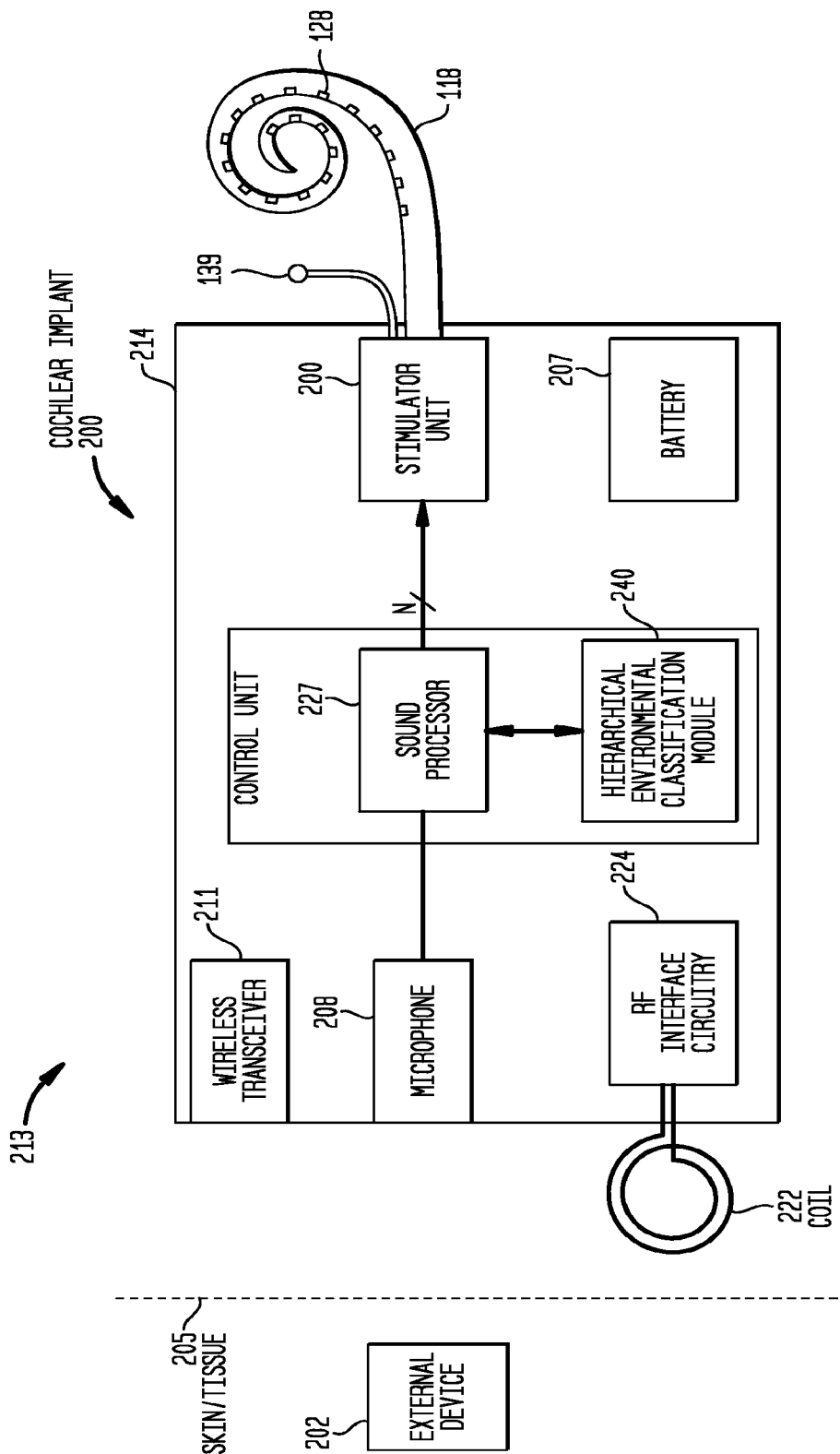
FIG. 2 is a block diagram of a totally implantable cochlear implant system, in accordance with certain embodiments presented herein.

FIGS. 1A-1C illustrate an arrangement in which the cochlear implant 100 includes an external component. However, it is to be appreciated that embodiments of the present invention may be implemented in cochlear implant systems having alternative arrangements. For example, FIG. 2 is a functional block diagram of an exemplary totally implantable cochlear implant 200 configured to implement embodiments of the present invention. Since the cochlear implant 200 is totally implantable, all components of cochlear implant 200 are configured to be implanted under skin/tissue 205 of a recipient. Because all components are implantable, cochlear implant 200 operates, for at least a finite period of time, without the need of an external device. An external device 202 can be used to, for example, charge an internal power source (battery) 207. External device 202 may be a dedicated charger or a conventional cochlear implant sound processor.

Cochlear implant 200 includes an implant body (main implantable component) 214, one or more input elements 213 for receiving sound signals (e.g., one or more implantable microphones 208 and a wireless transceiver 211), an implantable coil 222, and an elongate intra-cochlear stimulating assembly 118 as described above with reference to FIG. 1. The microphone 208 and/or the implantable coil 222 may be disposed in, or electrically connected to, the implant body 214. The implant body 214 further comprises the battery 207, RF interface circuitry 224, a control unit 225, and a stimulator unit 220 (which is similar to stimulator unit 120 of FIGS. 1A-1C). The control unit 225 may be similar to control unit 125 of FIGS. 1A-1C and includes a sound processor 227 and a hierarchical environmental classification module 240.

The one or more implantable microphones 208 are configured to receive sound signals. The sound processor 227 is configured to execute sound processing and coding to convert the received/detected sound signals (e.g., received by microphone 208) into processed sound signals 231. As noted above, FIGS. 1A and 1B illustrate an embodiment in which the external component 102 includes the sound processor 127. As such, in the illustrative arrangement of FIGS. 1A and 1B, the processed sound signals 131 are provided to the implanted stimulator unit 120 via the RF link between the external coil 106 and the internal coil 122. However, in the embodiment of FIG. 2 the sound processor 227 is implanted in the recipient. As such, in the embodiments of FIG. 2, the processed sound signals 231 do not traverse the RF link, but instead are provided directly to the stimulator unit 220. The stimulator unit 220 is configured to utilize the processed sound signals 231 to generate electrical stimulation signals that are delivered to the recipient's cochlea via one or more stimulation channels.

As noted, implant body 214 includes the hierarchical environmental classification module 240. Similar to the arrangement of FIGS. 1A-1C, the hierarchical environmental classification module 240 is configured to evaluate/analyze attributes of a set of input sound signals received by the one or more input elements (e.g., implantable microphones 208 or wireless transceiver 211) and, based on the analysis, determine a plurality of "hierarchical classifications" for the set of sound signals.

The hierarchical environmental classification techniques presented herein may be implemented in a number of different hearing prosthesis, such as hearing prostheses that include external components, totally implantable hearing prostheses, etc. However, for ease of description, further details of the hierarchical environmental classification techniques will generally be described with reference to cochlear implant 100 of FIGS. 1A-1C.

More specifically, FIG. 3A is a functional block diagram illustrating further details of the sound processing unit 112 of cochlear implant 100. For ease of illustration, elements that are not related to the sound processing and hierarchical environmental classification techniques have been omitted from FIG. 3A.

As noted, the cochlear implant 100 comprises one or more input elements 113. In the example of FIG. 3A, the input elements 113 comprise a first microphone 108A, a second microphone 108B, and at least one auxiliary input 115 (e.g., an audio input port, a cable port, a telecoil, a wireless transceiver, etc.). If not already in an electrical form, sound input elements 113 convert received/input sound signals into electrical signals 153, referred to herein as electrical input signals, which represent the received sound signals. As shown in FIG. 3A, the electrical input signals 153 include electrical input signal 153A from microphone 108A, electrical input signal 153B from microphone 108B, and electrical input signal 153C from auxiliary input 115. The electrical input signals 153 are provided to a pre-filterbank processing module 154.

The pre-filterbank processing module 154 is configured to, as needed, combine the electrical input signals 153 received from the sound input elements 108 and prepare those signals for subsequent processing. The pre-filterbank processing module 154 then generates a pre-filtered output signal 155 that, as described further below, is the basis of further processing operations. The pre-filtered output signal 155 represents the collective sound signals received at the sound input elements 108 at a given point in time.

The sound processing unit 112 includes a sound processor 127 that is generally configured to execute sound processing and coding to convert the pre-filtered output signal 155 into output signals that represent electrical stimulation for delivery to the recipient. In the general, the sound processor 127 performs represents a series of operations performed by the one or more processors 137 executing sound processing logic 135 from memory 162 of the control unit 125 (FIG. 1C). In FIG. 3A, the operations of the sound processor 127 are represented by blocks 154, 156, 158, 160, and 162, which collectively comprise a sound processing path 151.

The sound processing path 151 comprises a filterbank module (filterbank) 156, a post-filterbank processing module 158, a channel selection module 160, and a channel mapping and encoding module 162. In operation, the pre-filtered output signal 155 generated by the pre-filterbank processing module 154 is provided to the filterbank module 156. The filterbank module 156 generates a suitable set of bandwidth limited channels, or frequency bins, that each includes a spectral component of the received sound signals. That is, the filterbank module 156 comprises a plurality of band-pass filters that separate the pre-filtered output signal 155 into multiple components/channels, each one carrying a frequency sub-band of the original signal (i.e., frequency components of the received sounds signal).

The channels created by the filterbank module 156 are sometimes referred to herein as sound processing channels, and the sound signal components within each of the sound processing channels are sometimes referred to herein as band-pass filtered signals or channelized signals. The band-pass filtered or channelized signals created by the filterbank module 156 are processed (e.g., modified/adjusted) as they pass through the sound processing path 151. As such, the band-pass filtered or channelized signals are referred to differently at different stages of the sound processing path 151. However, it will be appreciated that reference herein to a band-pass filtered signal or a channelized signal may refer to the spectral component of the received sound signals at any point within the sound processing path 151 (e.g., pre-processed, processed, selected, etc.).

At the output of the filterbank module 156, the channelized signals are initially referred to herein as pre-processed signals 157. The number 'in' of channels and pre-processed signals 157 generated by the filterbank module 156 may depend on a number of different factors including, but not limited to, implant design, number of active electrodes, coding strategy, and/or recipient preference(s). In certain arrangements, twenty-two (22) channelized signals are created and the sound processing path 151 is said to include 22 channels.

The pre-processed signals 157 are provided to the post-filterbank processing module 158. The post-filterbank processing module 158 is configured to perform a number of sound processing operations on the pre-processed signals 157. These sound processing operations include, for example, channelized gain adjustments for hearing loss compensation (e.g., gain adjustments to one or more discrete frequency ranges of the sound signals), noise reduction operations, speech enhancement operations, etc., in one or more of the channels. After performing the sound processing operations, the post-filterbank processing module 158 outputs a plurality of processed channelized signals 159.

In the specific arrangement of FIG. 3A, the sound processing path 151 includes a channel selection module 160. The channel selection module 160 is configured to perform a channel selection process to select, according to one or more selection rules, which of the 'm' channels should be use in hearing compensation. The signals selected at channel selection module 160 are represented in FIG. 3A by arrow 161 and are referred to herein as selected channelized signals or, more simply, selected signals.

In the embodiment of FIG. 3A, the channel selection module 156 selects a subset 'n' of the 'm' processed channelized signals 159 for use in generation of electrical stimulation for delivery to a recipient (i.e., the sound processing channels are reduced from 'm' channels to 'n' channels). In one specific example, the 'n' largest amplitude channels (maxima) from the 'm' available combined channel signals/masker signals is made, with 'm' and 'n' being programmable during initial fitting, and/or operation of the prosthesis. It is to be appreciated that different channel selection methods could be used, and are not limited to maxima selection.

It is also to be appreciated that, in certain embodiments, the channel selection module 160 may be omitted. For example, certain arrangements may use a continuous interleaved sampling (CIS), CIS-based, or other non-channel selection sound coding strategy.

The sound processing path 151 also comprises the channel mapping module 162. The channel mapping module 162 is configured to map the amplitudes of the selected signals 161 (or the processed channelized signals 159 in embodiments that do not include channel selection) into a set of output signals (e.g., stimulation commands) that represent the attributes of the electrical stimulation signals that are to be delivered to the recipient so as to evoke perception of at least a portion of the received sound signals. This channel mapping may include, for example, threshold and comfort level mapping, dynamic range adjustments (e.g., compression), volume adjustments, etc., and may encompass selection of various sequential and/or simultaneous stimulation strategies.

In the embodiment of FIG. 3A, the set of stimulation commands that represent the electrical stimulation signals are encoded for transcutaneous transmission (e.g., via an RF link) to an implantable component 104 as the processed sound signals 131 (FIG. 1B). This encoding is performed, in the specific example of FIG. 3A, at the channel mapping module 162. As such, channel mapping module 162 is sometimes referred to herein as a channel mapping and encoding module and operates as an output block configured to convert the plurality of channelized signals into a plurality of output signals 163.

FIG. 3A also illustrates the hierarchical environmental classification module 140 and the memory 162. For ease of description, the hierarchical environmental classification module 140 is described as a stand-alone element that is separate from memory 162. However, as noted above, the hierarchical environmental classification module 140 may comprise logic (software) stored in memory 162 that is executable by one or more processors 135 (FIG. 1C).

The hierarchical environmental classification module 140 (e.g., the processors 135 executing hierarchical environmental classification logic 140 stored in memory 162) is configured to evaluate/analyze attributes of a set of input sound signals and, based on the analysis, determine a "hierarchical classification" for the set of sound signals. As used herein, a "hierarchical classification" is a set of linked/interrelated "nested" classifications that are generated from the same set of sound signals, yet represent different characteristics of the sound signals. A set of hierarchical classifications includes a "primary" or "principal" classification and one or more "secondary" or "derivative" classifications that are "nested" together. As used herein, one or more secondary classifications are "nested" with an associated principle classification when the one or more secondary classifications are encompassed by the associated primary classification (i.e., an overlapping and non-mutually exclusive relationship) and the one or more secondary classifications sub-categorize the associated primary classification (i.e., further qualify specific characteristics/attributes of the primary classification). As described further below, the primary classification represents a basic categorization of the sound environment (e.g., the ambient environment in which the cochlear implant 100 is located and/or of the environment of the received sound signals), while the one or more secondary classifications define sub-categories of the associated primary classification and, in certain examples, of other secondary classifications. As described further below, the hierarchical environmental classification module 140 generates a hierarchical classification output 161 that represents/includes the determined hierarchical classification for the set of sound signals.

As shown in FIG. 3A, the hierarchical classification output 161 is stored in memory 162. Over time, a plurality of the hierarchical classification outputs 161 are generated by the hierarchical environmental classification module 140 and stored in memory 162 to form a hierarchical classification data set/log 164. As described further below, the hierarchical classification data set 164 may be used for a number of different purposes. In one embodiment, the hierarchical classification data set 164 may be used to set or adjust one or more parameters of the cochlear implant 100 and, accordingly, improve performance of the cochlear implant 100.

More specifically, the hierarchical environmental classification module 140 (e.g., the processors 135 executing hierarchical environmental classification logic 140 stored in memory 162) or another processing module distinct from the classification module, such as one designed only to analyze the data logs, is configured to analyze the hierarchical classification data set 164 that is generated over a time period (e.g., a second, a minute, a hour, a day, a week, a month, etc.) from a number of different sets of sound signals received at the sound inputs 108. The analyzed time frame may vary and, in certain examples, sound processing options might be adjusted within a very short time frame (e.g. a few seconds), based on short term factors (e.g., gain needs for to reaction to a particular sound). Over a longer period of time, the logged data can provide information about the environments or longer term trends, thus the resulting adjustments may be viewed as "fine tuning" rather than reactive to a specific event. The data logs may also be analyzed by a clinical specialist or machine learning algorithm to determine trends, identify issues, etc. Some examples of a slow reaction might be to analyze the datalogs over many days and look at how much external voice has been captured, compared to other input signals such as noise and music. From this information, the analysis could decide if the sound path should be optimized to emphasize speech more, over other signals (e.g., with a greater amount of speech enhancement or noise reduction). Alternatively, if music is a much higher percentage than external or own voice, then perhaps optimize the sound path for a more music based signal input, rather than speech. Such changes would rely upon data collected over a long time period.

As noted, based on this analysis (represented in FIG. 3A by arrow 163), the hierarchical environmental classification module 140 may automatically adapt/adjust one or more operations of the sound processing path 151 based on the hierarchical classification data set 164 (i.e., based on the nested classifications generated, over time, including within the data set). As represented by dashed arrows 165, the hierarchical environmental classification module 140 may adjust operations of the pre-filterbank processing module 154, the filterbank module 156, the post-filterbank processing module 158, the channel selection module 160, and/or the mapping and encoding module 162 to adjust how output signals, representative of stimulation, are generated by the cochlear implant 100. As such, in certain embodiments, the stimulation delivered to the recipient is based on the nested classifications generated, over time, which are stored as part of the hierarchical classification data set 164. In other words, the hierarchical environmental classification module 140 may be configured to implement an automated learning or adaption process to adjust settings/parameters of the sound processor 127 in response to different environmental conditions may (i.e., the prosthesis learns the appropriate settings in the presence of certain categories and sub-categories).

In the example of FIG. 3A, the operations of the hierarchical environmental classification module 140 are performed using electrical input signal 153A from microphone 108A. In certain embodiments, the microphone 108A is a front-facing omnidirectional microphone that provides a full set of speech input from all directions. However, it is to be appreciated that the hierarchical environmental classification module 140 may generate the hierarchical classifications using other versions of the received sound signals, such as the pre-filtered output signal 155 generated by the pre-filterbank processing module 154, the pre-processed signals 157, electrical signal 153C from the auxiliary input (e.g., a signal from a wired or wireless accessory), other audio signals available in the cochlear implant 100, and/or combinations thereof.

Figure 3B:
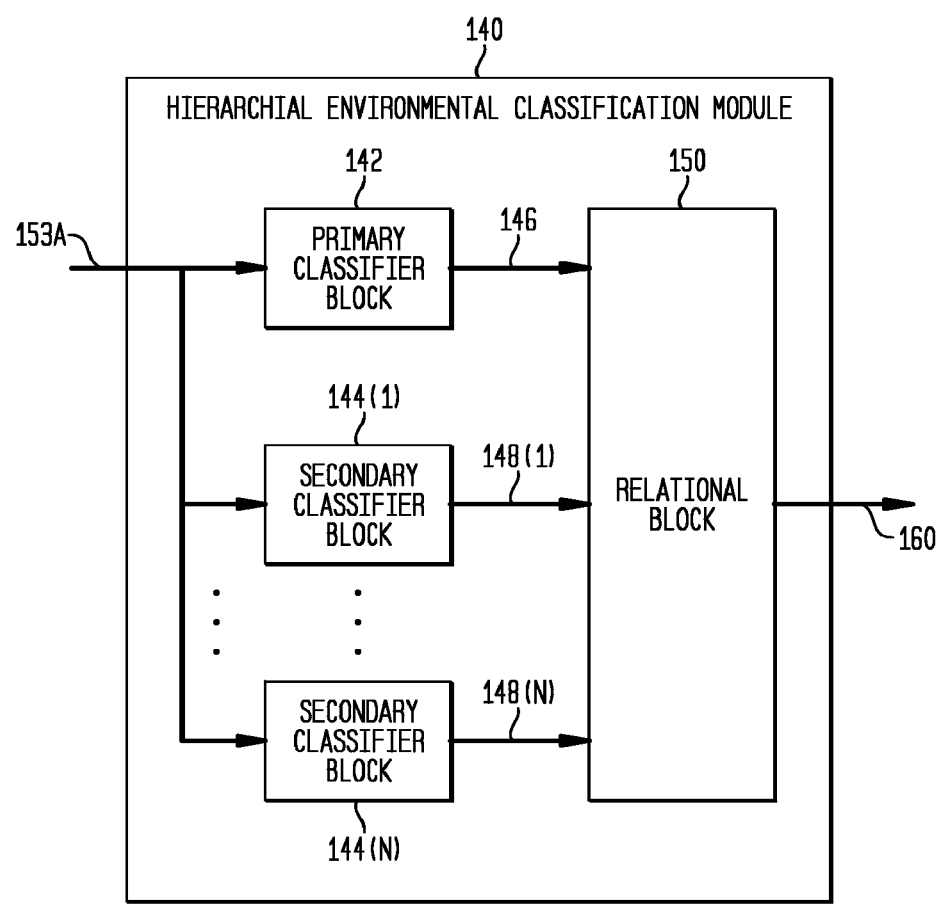
FIG. 3B is a functional block diagram illustrating further details of a hierarchical environmental classification module, in accordance with certain embodiments presented herein.

FIG. 3B is a functional block diagram illustrating further details of the hierarchical environmental classification module 140 of FIG. 3A. As shown, the hierarchical environmental classification module 140 includes a primary classifier block 142 and a plurality of secondary classifier blocks 144(1)-144(N). The primary classifier block 142 and the plurality of secondary classifier blocks 144(1)-144(N) are sometimes collectively referred to herein as "hierarchical classifier blocks" because each of the sub-categorizations made by the secondary classifier blocks 144(1)-144(N) are a derivative or function of one or more of the primary categorizations made by the primary classifier block 142 (i.e., multiple classification structures that are operationally linked to one another). That is, as described further below, the primary classifier block 142 and the plurality of secondary classifier blocks 144(1)-144(N) each perform a specific type of classification, but the secondary classifications by the secondary classifier blocks 144(1)-144(N) are related to (i.e., a sub-categorization of) at least one of the primary classifications and, in certain embodiments, one or more of the other secondary classifications.

In accordance with certain embodiments presented herein, the primary classifier block 142 is configured to use a set of sound signals to "classify" or "categorize" the sound environment of the sound signals. The primary classifier block 142 may be configured to categorize the sound environment into a number of classes/categories. In one illustrative example, the primary classifier block 142 is configured to categorize the sound environment into one of six (6) categories, including "Speech," "Noise," "Speech in Noise," "Music," "Wind," and "Quiet."

In certain embodiments, the primary classifier block 142 and the secondary classifier blocks 144(1)-144(N) each operates to determine a category or sub-category for the set of sound signals using a type of decision structure (e.g., decision tree) that extracts a plurality of features from the incoming sound signals, analyzes (e.g., compares) values of the extracted signal features relative to pre-determined values (e.g., compares feature values to pre-determined thresholds), and determines, based on the results of the analysis, the most likely category or sub-category for the set of sound signals.

The plurality of signal features that are extracted from the set of sound signals within the primary classifier block 142 and each of the secondary classifier blocks 144(1)-144(N) depends on the specific classification/categorization to be made by the associated classifier block. For example, the primary classifier block 142 may extract signal features such as amplitude modulations, spectral profile, harmonicity, amplitude onsets, etc., while the secondary classifier blocks 144(1)-144(N) may extract the same or different signal features. It is also to be appreciated that the primary classifier block 142 and/or one or more of the secondary classifier blocks 144(1)-144(N) may extract overlapping sets of signal feature or different signal features.

As noted, after the extraction of signal features, the primary classifier block 142 and each of the secondary classifier blocks 144(1)-144(N) analyzes the associated extracted signal features to generate a determination as to a specific categorization of the set of sound signals from which the features were extracted. In general, the determination by a classifier block is a mapping from the feature space to a decision space where, for every point in the feature space, a corresponding category is defined. The borders between the classes/sub-classes are generally found through pre-training using sound data. The determination may make use of, for example: rule-based classification (e.g., where boundaries between the classes are lines orthogonal to the feature axes); minimum-distance classification (e.g., where the distance of an observation to all classes is measured, and the class with the shortest distance is chosen); Bayes classification (e.g., classification using histograms of class-specific probabilities), one or more neural networks, one or more Hidden Markov models (HMMs), etc.

As noted, the primary classifier block 142 and each of the secondary classifier blocks 144(1)-144(N) generate an associated specific classification. The primary classification generated by the primary classifier block 142 is represented in FIG. 3B by arrow 146, while the secondary classifications made by the secondary classifier blocks 144(1)-144(N) are represented in FIG. 3B by arrows 148(1)-148(N), respectively.

In certain examples, the primary classifier block 142 and each of the secondary classifier blocks 144(1)-144(N) are separate classifiers that operate independently and in parallel to generate the respective primary classification 146 and secondary classifications 148(1)-148(N). In other embodiments described further below, the secondary classifier blocks 144(1)-144(N) may operate in a plurality of time-delayed stages where certain one or more of the secondary classifier blocks 144(1)-144(N) are only activated in response to a particular primary classification 146 or particular other secondary classification 148(1)-148(N) (e.g., save processing cycles by calculating the sub-categories only when the primary classifier block identifies a specific primary classification and/or could be pre-empted ahead of time based on a rising probability likely to lead to the primary classifier block determining a new primary classification). In still other embodiments, the primary classifier block 142 and the each of the secondary classifier blocks 144(1)-144(N) may be part of a single multi-stage classifier that can generate both the primary and secondary classifications either in parallel or in a plurality of time-delayed stages.

In the example of FIG. 3B, the hierarchical environmental classification module 140 includes a relational block 150 that analyzes the primary classification 146 and the secondary classifications 148(1)-148(N) relative to one another. In particular, the relational block 150 is configured to use one or more of the secondary classifications 148(1)-148(N) to sub-categorize the primary classification 146. Stated differently, the relational block 150 operates to associate one or more of the secondary classifications 148(1)-148(N) with the primary classification and, as a result, define specific characteristics of the sound environment that is represented by the primary classification. The relational block 150 may also use at least one of the secondary classifications 148(1)-148(N) to sub-categorize one or more other of the secondary classifications 148(1)-148(N) (i.e., the relational block 150 may operate to associate one or more of the secondary classifications 148(1)-148(N) with one or more other of the secondary classifications). In certain examples, the secondary classification (e.g., own versus external speech) is only "recorded" by the relational block 150 when the primary classification is "speech." Similarly for other categories and sub-categories The relational block 150 generates the hierarchical classification output 161 that, as noted above, includes the determined hierarchical classification for the set of sound signals. Also as noted above, the hierarchical classification output 161 is stored in memory 162 as part of a hierarchical classification data set 164. Further details regarding analysis of the hierarchical classification data set 164 are described further below. In addition, further understanding of the operations of the hierarchical environmental classification module 140 and analysis of hierarchical classification data set 164 may be appreciated through the following illustrative examples.

Referring first to FIG. 4A, shown is a schematic diagram of a hierarchical classification structure 455 that may be implemented within a hierarchical environmental classification module, such as hierarchical environmental classification module 140, in accordance with embodiments presented herein. In this example, the hierarchical classification structure 455 includes five (5) primary classifications 446 of the sound environment. The five primary classifications 446 comprise a "Speech" classification 446(1), a "Speech in Noise" classification 446(2), a "Music" classification 446(3), a "Quiet" classification 446(4), and a "Noise" classification 446(5). These five primary classifications represent the five types of sound environments that the associated hearing prosthesis can detect, in this particular example, from a set of sound signals. That is, in this example, a hierarchical environmental classification module includes a primary classification block that is configured to analyze a set of sound signals to determine which of these five environments the hearing prosthesis is located when the set of sound signals are received. As described elsewhere herein, these specific sound environment classifications are illustrative.

In the example of FIG. 4A, the hierarchical classification structure 455 also includes two (2) secondary classifications 448. The two secondary classifications comprise an "Own Voice" classification 448(1) and an "External Voice" classification 448(2). The Own Voice classification 448(1) and the External Voice classification 448(2) are each derivative of, and further define, both the Speech classification 446(1) and the Speech in Noise classification 446(2). That is, if the primary classifier determines that the hearing prosthesis is located in either a Speech environment or a Speech in Noise environment, then the environment is sub-categorized as either Own Voice (i.e., the hearing prosthesis recipient is speaking within the set of sound signals) or as External Voice (i.e., someone other than the hearing prosthesis recipient is speaking within the set of sound signals).

In the embodiment of FIG. 4A, the Own Voice classification 448(1) and the External Voice classification 448(2) are generated by a single secondary classifier block. As such, FIG. 4A represents an embodiment in which a hierarchical environmental classification module includes one primary classifier block that has five associated categorizations and one secondary classifier block having two associated sub-categorizations. As described elsewhere herein, the use of only one secondary classifier block is illustrative and that other embodiments may include multiple primary classifications and/or multiple secondary classifiers. It is also to be appreciated that the embodiments presented herein may include more than two levels of classification.

As noted, a primary classification 446 and, in certain circumstances, a secondary classification 448, is generated for a single set of sound signals (i.e., one or more sounds detected/received by sound inputs of the hearing prosthesis). Over time, a plurality of different sets of sound signals may be detected by the sound inputs of the hearing prosthesis. Accordingly, over time, the hierarchical environmental classification module may also generate a plurality of primary classifications 446 from different sets of sound signals and, depending thereon, a plurality of secondary classification 448, that are stored (e.g., in memory) as part of a hierarchical classification data set (e.g., hierarchical classification data set 164 of FIG. 3A).

Figure 4B:
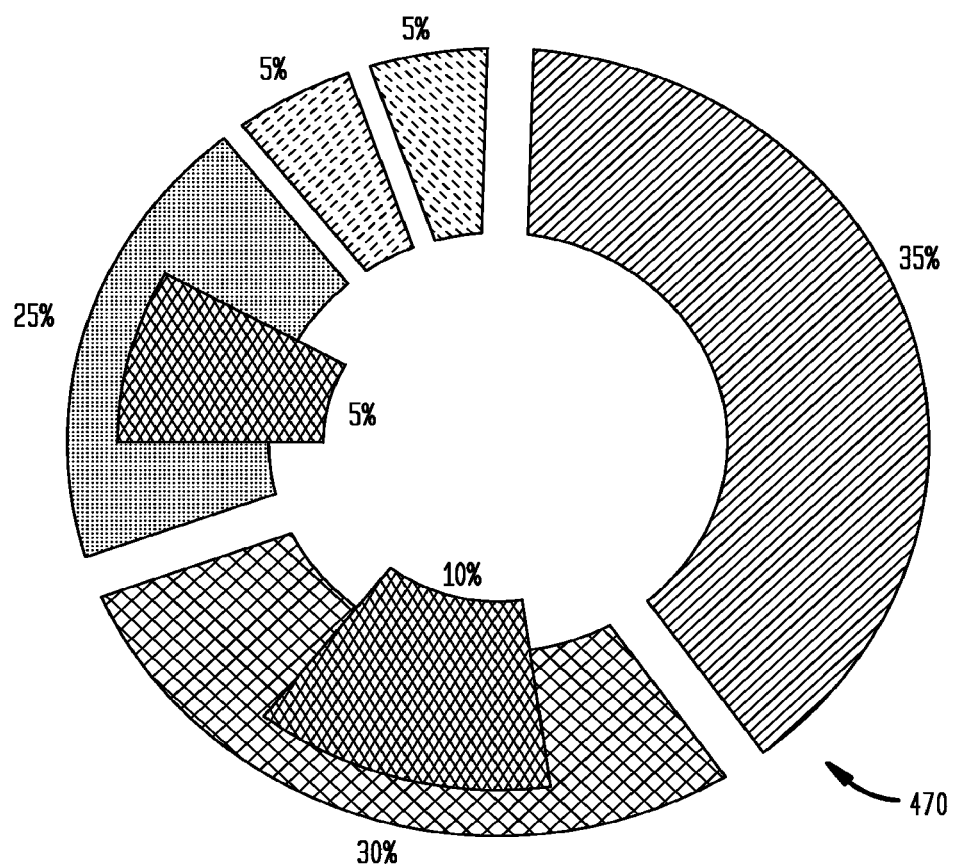
FIG. 4B is an schematic diagram illustrating example informational content of an hierarchical classification data set generated, over a period of time, in accordance with one embodiment of FIG. 4A.

FIG. 4B is an schematic diagram illustrating the informational content of an hierarchical classification data set generated, over a period of time, in accordance with the embodiment of FIG. 4A. More specifically, FIG. 4B includes a doughnut chart 470 which shows example classifications made for the hearing prosthesis analyzed in accordance with FIG. 4A over a time period (total usage time). In this example, the hearing prosthesis is located in: (1) a Speech class 30% of the time period, (2) a Quiet class 35% of the time period, (3) a Speech in Noise class 25% of the time period, (4) a Noise class 5% of the time period, and (5) a Music class 5% of the time period, which are each determined as a primary classification 446 (FIG. 4A). By adding the secondary classifications 448 (FIG. 4A), it can be seen that, while in the Speech class, the hearing prosthesis detected Own Speech 10% of that time (i.e., 10% of the 30%) and, while in the Speech in Noise class, the hearing prosthesis detected Own Speech 5% of that time (i.e., 5% of the 25%). It is to be appreciated that these specific percentages are merely illustrative the primary and secondary classifications that can form part of a hierarchical classification data set in accordance with embodiments presented herein.

As detailed above, a hierarchical classification data set represents the primary classifications (i.e., the type of sound environments) and any derivative secondary classifications of the primary classifications (i.e., any sub-categories of the different sound environments) identified during a time period. The hierarchical classification data set can be used for a number of different purposes to improve the operation of the associated hearing prosthesis.

For example, it has been shown that children's linguistic and cognitive development is strongly dependent upon their language environment. Quantitative features of caregiver language, such as the number of words addressed to children recipients and the amount of conversational turns in which they participate have proven to be good predictors of the children's developmental trajectory. Similarly, for elderly recipients, the amount of produced speech can be a relevant metric to evaluate their speech communication capabilities. In conventional arrangements, quantifying such features of the natural language environment is time consuming and costly, thus limiting the observations to a few hours per recipient.

The techniques presented herein increase the scientific and clinical value of automated auditory scene classification within hearing prostheses, such as for cases in which the detection of the wearer's own voice will be crucial. In these scenarios, the techniques presented herein are able to log different important features of the linguistic experience, including the amount of own speech (which is a good indicator of language development). The amount of caregiver's speech and the number of conversational turns reflect the quality and adequacy of the language input. Both measures can provide an indication of the recipient's social integration and participation and can provide clinicians with important information to guide their therapy and help researchers to increase knowledge about the everyday experience of people with hearing prostheses. The indication of the recipient's social integration and participation could take any of a number of different forms (e.g., data reports, etc.) for presentation to the to the parents, caregivers, clinicians, etc.

As such, a hierarchical classification data set generated in accordance with embodiments presented herein may be used as a tool for analyzing the characteristics/attributes of the sound environments in which a hearing prosthesis is used by a hearing prosthesis recipient. This analysis may enable adjustments to the operation of the hearing prosthesis that are specifically tailored to the recipient and/or for other purposes. In one example, a hierarchical classification data set enables the determination of the amount of speech produced over time, which operates as a tool for language development monitoring and/or as a tool for monitoring of auditory diet (i.e., listening) so that clinician/language pathologist can guide the therapy and can give proper advice to the recipient, parent, caregiver, etc. A hierarchical classification data set may also or alternatively be used for detection of poor quality speech input, monitoring language development through, for example, mean length of utterance (MLU), analysis of conversational turns, analysis of language complexity, etc.

In one specific example, a hierarchical classification data set may be used to analyze a recipient's "time-on-air," meaning how often the recipient speaks (i.e., how often Own Voice is detected). This time-on-air determination may be correlated with the amount of time the recipient is in a speech-related environment (e.g., a Speech environment, a Speech in Noise environment, etc.), for example. This correlation may indicate when a recipient is withdrawn, makes less use of the hearing prosthesis than normal, etc. The correlation of the time-on-air and the speech-related environment may be used to initiate one or more diagnostic operations. These diagnostic operations may include, for example, evaluation of coil-off time (and possible number of occurrences), evaluation of compliance of current source, impedance measurements (to check for fluctuating impedances), etc. One or more of these diagnostic operations could be checked against environments to see whether these events cause people to avoid situations they might not otherwise avoid (e.g., is there less than the usual time in speech or music that is also correlated with one or more of the above diagnostic conditions occur).

As noted above, in certain embodiments, a hierarchical classification data set can be used to adjust/set parameters or settings (e.g., noise reduction settings, tinnitus masking settings, microphone settings, gain settings, channel dynamic range, maxima selection, comfort settings, etc.) within the hearing prosthesis itself, such as operations of the sound processing path. For example, the selection of certain settings by the recipient could be logged (i.e., log when the settings are turned on and off). The recipient's use of the settings during a time period may be analyzed relative to the attributes of the sound environments in which the settings are used during the time period to obtain insight into the recipient's preferences in response to different environmental conditions. This information may then be used to adapt operation of the hearing prosthesis to the recipient's preferences. For example, as noted above, the recipient's use of the settings in response to different environmental conditions may be used as part of an automated learning or adaption process implemented by the hearing prosthesis (i.e., the prosthesis learns the appropriate settings in the presence of certain categories and sub-categories).

In still other examples, a hierarchical classification data set can be used to analyze the use of accessories by a recipient. For example, the hearing prosthesis could detect when an accessory (e.g., wireless microphone, etc.) is in use and correlate this information with the information in the hierarchical classification data set. In one illustrative example, if the use of an accessory is associated with an increase in conversational speech, or perhaps greater exposure to external speech, then this may indicate that accessory use is helpful for increasing exposure to speech and encouraging conversational turns (e.g., in children).

In another example, when the recipient's own voice is detected, the hearing prosthesis could operate to reduce the gain so that the user's own voice is not too loud for their own listening. In yet another example, if a primary classification of "music: class is broken down into different genres, then appropriate actions could be initiated to tailor the prosthesis settings to the specific type of music or the recipient preferences (e.g., a secondary classification of "Jazz" could result in an immediate gain reduction, if the previous indications have indicated that the recipient does not prefer Jazz music). In a another example, the hearing prosthesis could operate to adapt the amount of noise reduction applied when in the "Speech in Noise" class to be less when own voice is detected, yet apply more noise reduction when an external voice is detected.

As noted, the specific primary and secondary classifications described above are illustrative and embodiments of the present invention may make use of a number of different primary or secondary classifications. For example, in addition to the primary classifications described above, additional or alternative primary classifications may include, but are not limited to, a "Wind" classification, a "Rain" classification, an "Animal" classification, a "Car" classification, an "Indoor" classification, an "Outdoor" classification, etc. Each of these primary classifications may also be sub-categorized in one or more manners (i.e., each may be associated with one or more secondary classifications). For example, the "Wind" classification may be sub-categorized as "high wind," "moderate wind," or "low wind," while the "Rain" classification may be sub-categorized as "Torrential rain," 'light rain," etc. The "Animal" classification and the "Car" classification may be sub-categorized into different animal types or car types, respectively. The "Indoor" classification could, in one example, be sub-categorized into room size, while the "Outdoor" classification could be sub-categorized into different natural environments (e.g., ocean/beach, forest, etc.). Again, these specific examples are illustrative.

Speech-related environments (e.g., a Speech classification, Speech in Noise classification, etc.) may be further sub-categorized based on attributes of the detected speech. As noted, two speech-based sub-categorizations are the Own Voice classification and the External voice classification described with reference to FIGS. 4A and 4B. Other example speech-based sub-categorizations include: (1) a "Male" classification (i.e., a determination that the speaker in a set of sound signals is a male), (2) a "Female" classification (i.e., a determination that the speaker in a set of sound signals is a female), (3) a "Child" classification (i.e., a determination that the speaker in a set of sound signals is a child), (4) an "Adult" classification (i.e., a determination that the speaker in a set of sound signals is an adult), (5) a "Monologue" classification (i.e., determination that the speech in a set of sound signals is part of an extended speech by a single individual), (6) a "Dialogue" classification (i.e., determination that the speech in a set of sound signals is part of a conversation between multiple individuals), (7) a "Near Speech" classification (i.e., speech is within a predetermined proximity to a recipient), (8) a "Distant Speech" classification (i.e., speech is outside of a predetermined proximity to a recipient), (9) an "Electronic Media" classification (i.e., the speech is from a television or other electronic media source), (10) a "Child Directed Speech" class, (11) a "Speaker identity" classification (i.e., a specific determination of the speaker, such as mother, father, etc.), etc. These speech-based sub-categorizations may be determined based, for example, on fundamental frequency analysis, vocal tract length analysis, etc.

In another example, a noise-related environment (e.g., a Noise classification, a Speech in Noise classification, etc.) may be further sub-categorized based on attributes of the detected speech. For example, a noise-related environment sub-categorization may be a "Noise type" classification. In these examples, the type of source of the noise in the set of sound signals may be categorized (e.g., as playground noise, classroom noise, traffic noise, machinery noise, etc.). Such information could provide the recipient, caregiver, or other user with information regarding how often the recipient is affected by noise and the likely cause/source, timing, etc. of the noise FIG. 5 is a schematic diagram illustrating additional example secondary classifications (sub-categories) in accordance with certain embodiments presented herein. More specifically, FIG. 5 illustrates a portion of a hierarchical classification structure 555 that may be implemented by a hierarchical environmental classification module, such as hierarchical environmental classification module 140, in accordance with embodiments presented herein. FIG. 5 illustrates a single primary classification 546(1), but it is to be appreciated that the hierarchical classification structure 555 also includes other primary classifications of the sound environment (e.g., Speech in Noise, Noise, Quiet, etc.) which, for ease of illustration, have been omitted from FIG. 5.

In the example of FIG. 5, the hierarchical classification structure 555 includes eight (8) secondary classifications 548 that are derivative from, and further define, the Speech classification 546(1). The secondary classifications are organized as two tiers/layers, 549(1) and 549(2). The first layer 549(1) includes six secondary classifications shown as a "Male" classification 548(1), a "Female" classification 548(2), an "Own voice" classification 548(3), an "External Voice" classification 548(4), an "Adult" classification 548(5), and a "Child" classification 538(6). That is, if the primary classifier block determines that the hearing prosthesis is located in a Speech environment, then the environment is sub-categorized in three different manners by three different secondary classifier blocks. In particular, at 548(1) and 548(2) a secondary classifier block (i.e., a Gender classifier block) determines the gender of the individual associated speech in the set of sound signals (i.e., determines whether the speaker is male or female). At 548(3) and 548(4), another secondary classifier block determines whether the speech in the set of sound signals is the recipient's own voice (i.e., the hearing prosthesis recipient is speaking within the set of sound signals) or whether the speech is external voice (i.e., someone other than the hearing prosthesis recipient is speaking within the set of sound signals). At 548(5) and 548(6), yet another secondary classifier block determines whether the speech in the set of sound is associated with a child or adult (i.e., determines whether the speaker is a child or an adult). Each of the secondary classifications may be made for a set of sound signals.

In the embodiment of FIG. 5, the seventh and either secondary classifications 548(7) and 548(8) are a "Monologue" classification and a Dialogue" classification, which are derivative from each of the "Own Voice" and "External voice" classifications 548(3) and 548(4). As noted above, the Monologue classification 548(7) indicates that the speech in the set of sound signals is part of a monologue (i.e., speech by a single individual) while the Dialogue classification 548(8) indicates that the speech in the set of sound signals is part of a dialogue (i.e., a conversation).

FIG. 5 represents an embodiment in which a hierarchical environmental classification module includes one primary classifier block and four secondary classifier blocks (i.e., one of the Male/Female classifications, one for the Own/External Voice classifications, one for the Adult/Child classifications, and one for the Monologue/Dialogue classification). As described elsewhere herein, the use of four secondary classifier blocks is illustrative and that other embodiments may include other numbers of secondary classifier blocks. FIG. 5 also illustrates an example that includes three levels of classification. It is also to be appreciated that the embodiments presented herein may include more than three levels of classification.

Figure 6:
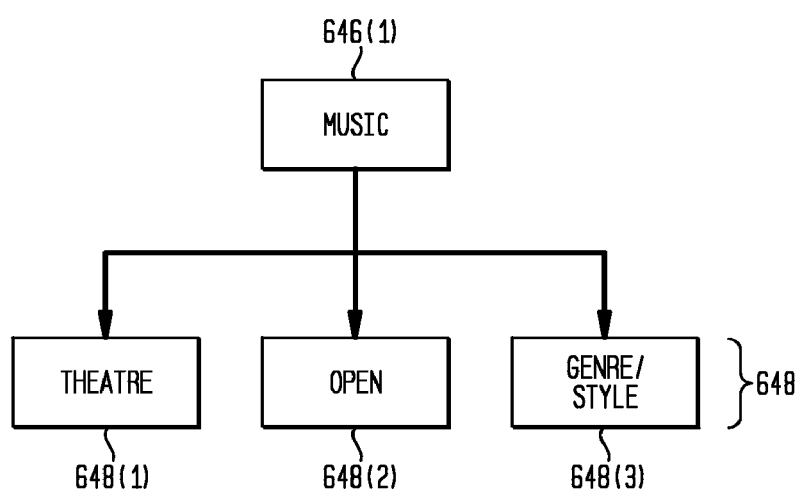

FIG. 6 is a schematic diagram illustrating further example secondary classifications (sub-categories) in accordance with certain embodiments presented herein. More specifically, FIG. 6 illustrates a portion of a hierarchical classification structure 655 that may be implemented by a hierarchical environmental classification module, such as hierarchical environmental classification module 140, in accordance with embodiments presented herein. FIG. 6 illustrates a single primary classification, namely a "Music" classification 646(1). However, it is to be appreciated that the hierarchical classification structure 655 also includes other primary classifications of the sound environment (e.g., Speech, Speech in Noise, Noise, Quiet, etc.) which, for ease of illustration, have been omitted from FIG. 6.

In the example of FIG. 6, the hierarchical classification structure 655 includes three (3) secondary classifications 648 that are derivative from, and further define, the Music classification 646(1). The three secondary classifications include a "Theatre" classification 648(1), an "Open" classification 648(2), and a "Genre/Style" classification 648(3). That is, if the primary classifier determines that the hearing prosthesis is located in a Music environment, then the environment is sub-categorized in at least three different manners. In particular, at 648(1), a secondary classifier block determines whether or not the music environment is a "Theatre" environment, while at 648(2) a secondary classifier determines whether or not the music environment is an open environment (e.g., an outdoor concert venue). At 648(3), a secondary classifier determines a genre or style of music detected in the set of sound signals. Each of the three secondary classifications 648(1), 648(2), and 648(3) may be made for the set of sound signals.

Figure 7:
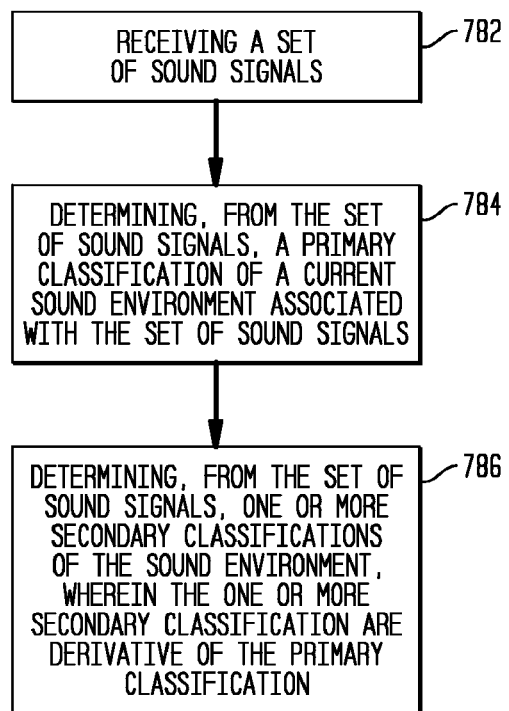
FIG. 7 is a flowchart of a method, in accordance with certain embodiments presented herein.

FIG. 7 is a flowchart of a method 780 in accordance with certain embodiments presented herein. Method 780 begins at 782 where a set of sound signals is received at one or more input elements of a hearing prosthesis. At 784, the hearing prosthesis determines, from the set of sound signals, a primary classification of a current sound environment associated with the set of sound signals. At 786, the hearing prosthesis determines, from the set of sound signals, one or more secondary classifications of the sound environment, wherein the one or more secondary classifications are derivative of the primary classification.

FIG. 8 is a flowchart of a method 890 in accordance with certain embodiments presented herein. Method 890 begins at 892 where a set of sound signals is received at one or more input elements of a hearing prosthesis. At 894, the set of sound signals are converted into one or more output signals for use in delivering stimulation to a recipient of the hearing prosthesis. At 896, a hierarchical classification of the set of sound signals is generated, wherein the hierarchical classification includes a plurality of nested classifications of a sound environment associated with the set of sound signals.

Many profoundly deaf children receive a cochlear implant early in life. Cochlear implants allow children who would not benefit from conventional hearing aids to access their auditory environment and acquire spoken language. However, the trajectories of these children's spoken language development vary widely. Some variation in the spoken language development of children with cochlear implants can be explained by differences in their auditory diet.

In general, normal hearing children's spoken language development is shaped by the language they are exposed to. Two important aspects of their language environment are (1) quantity of exposure and (2) interactivity. Young language learners must process large quantities of speech to correctly map words to meanings and extract patterns and rules. Interactivity is needed to guide the learner's attention, tailor the input to the child's needs and convey the social-pragmatic aspects of language use. Children with cochlear implants have the same needs, but they face additional difficulties that increase their risk for receiving insufficient language exposure.

First, cochlear implant recipients are more vulnerable to noise. Noise severely affects the speech understanding of cochlear implant users and, as such, reduces the amount of analyzable speech input and hampers incidental learning from overheard speech. When listening in noise, cochlear implant recipients also have to expend more cognitive resources, which leaves fewer resources for other tasks and causes listening fatigue. At the same time, noise is virtually omnipresent in children's home and school environments. Second, interactions between parents and children can be affected by the child's hearing impairment. Infants with a cochlear implant may respond differently to child-directed speech, and hearing adults can be unsure how to interact with a hearing impaired child. Such disruptions can further reduce the quantity and interactivity of language exposure.

Sufficient speech input and interactive communicative experiences are what drives spoken language development. Yet, young children with cochlear implants run a high risks of missing out on both of these experiences. At the same time young children with cochlear implants cannot fully advocate for themselves. Consequently, their caregivers should monitor their auditory environment, identify risks and intervene where necessary. The hierarchical environment classification techniques presented herein enable this monitoring with a level of specificity that is not available in conventional techniques. In particular, the use of secondary classifications to sub-categorize the basic sound environments provide recipients, caregivers, clinicians or other users with a better understanding of the attributes of the sound environments encountered by a recipient. The techniques presented herein may be used to, for example, distinguish child-directed speech and child speech, determine the child's own language production, infer the quantity and interactivity of caregiver-child communication, etc. The amount of speech produced by the child could help to assess the child's language development, and, as noted above, quantity and interactivity of speech are key indicators of the conduciveness of its environment.

It is to be appreciated that the above described embodiments are not mutually exclusive and that the various embodiments can be combined in various manners and arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The invention claimed is:

1. A method, comprising:
   receiving a set of input signals;
   determining, with a first classifier, a first classification of the set of input signals;
   conditionally activating a second classifier based on the first classification; and
   determining, using the second classifier, at least one second classification of the set of input signals, wherein the at least one second classification is a sub-category of the first classification.

2. The method of claim 1, further comprising:
   generating a classification output representing the first classification and the at least one second classification; and
   storing the classification output as part of a classification data set.

3. The method of claim 1, further comprising:
   adjusting one or more settings of a device based on the first classification and the at least one second classification.

4. The method of claim 3, wherein the device is a hearing device, and wherein the one or more settings comprise at least one of: noise reduction settings, tinnitus masking settings, microphone settings, gain settings, channel dynamic range, maxima selection, and comfort settings.

5. The method of claim 1, wherein the first classification is a classification of an ambient environment.

6. The method of claim 5, wherein the first classification indicates that the ambient environment is an environment that includes speech, and wherein determining the at least one second classification comprises:
   sub-categorizing the ambient environment based on attributes of the speech.

7. The method of claim 5, wherein the first classification indicates that the ambient environment is an environment that includes noise, and wherein determining the at least one second classification comprises:
   sub-categorizing a type of noise in the ambient environment.

8. The method of claim 1, further comprising:
   generating, based on the set of input signals, stimulation signals for delivery to a recipient of a medical device.

9. A device, comprising:
   one or more input elements configured to receive at least one set of environmental signals;
   a memory; and
   one or more processors coupled to the memory and the one or more input elements, and configured to:
   convert the at least one set of environmental signals into one or more output signals for use in delivering stimulation to a recipient of the device;
   determine a primary classification of the at least one set of environmental signals as a first classification; and
   in response to determining the primary classification of the at least one set of environmental signals as the first classification, determine a secondary classification of the at least one set of environmental signals as a second classification to generate a complex classification comprising a plurality of nested classifications of an ambient environment associated with the at least one set of environmental signals.

10. The device of claim 9, wherein the one or more processors are configured to determine an additional secondary classification of the at least one set of environmental signals as a third classification in response to determining the secondary classification of the at least one set of environmental signals is the second classification, wherein the third classification sub-categorizes the second classification.

11. The device of claim 9, wherein the first classification indicates that the ambient environment is an environment that includes speech, and wherein to determine the secondary classification, the one or more processors are configured to:
   sub-categorize the ambient environment based on attributes of the speech.

12. The device of claim 9, wherein the first classification indicates that the ambient environment is an environment that includes noise, and wherein to determine the secondary classification, the one or more processors are configured to:
   sub-categorize a type of noise in the ambient environment.

13. The device of claim 9, wherein the one or more processors are configured to:
   generate a classification output representing the plurality of nested classifications; and
   store the classification output as part of a classification data set in the memory.

14. The device of claim 9, wherein the one or more processors are configured to:
   automatically adjust one or more settings of the device based on the plurality of nested classifications.

15. The device of claim 14, wherein the one or more settings comprise at least one of:
   noise reduction settings, tinnitus masking settings, microphone settings, gain settings, channel dynamic range, maxima selection, and comfort settings.

16. The device of claim 9, wherein the one or more processors are configured to:
   block determination of the secondary classification of the at least one set of environmental signals in response to determining the primary classification of the at least one set of environmental signals is a third classification.

17. One or more non-transitory computer readable storage media comprising instructions that, when executed by a processor, cause the processor to:
   obtain a plurality of input signals;
   perform a first classification of the plurality of input signals; and
   conditionally perform at least one second classification of the plurality of input signals based on the first classification, wherein the at least one second classification is a sub-category of the first classification.

18. The one or more non-transitory computer readable storage media of claim 17, further comprising instructions operable to:
- generate a classification output representing the first classification and the at least one second classification; and
- store the classification output as part of a classification data set in memory.

19. The one or more non-transitory computer readable storage media of claim 17, further comprising instructions operable to:
- adjust one or more settings of a device based on the first classification and the at least one second classification.

20. The one or more non-transitory computer readable storage media of claim 17, further comprising instructions operable to:
- generate at least one output signal based on the plurality of input signals.

* * * * *